(12) United States Patent  
Allred

(10) Patent No.: US 7,281,799 B2
(45) Date of Patent: Oct. 16, 2007

(54) CORNEAL TOPOGRAPHY SLIT IMAGE ALIGNMENT VIA ANALYSIS OF HALF-SLIT IMAGE ALIGNMENT

(75) Inventor: Lloyd Allred, Bountiful, UT (US)

(73) Assignee: Bausch & Lomb Incorporated, Rochester, NY (US)

(*) Notice: Subject to any disclaimer, the term of this patent is extended or adjusted under 35 U.S.C. 154(b) by 279 days.

(21) Appl. No.: 11/186,733

(22) Filed: Jul. 21, 2005

(65) Prior Publication Data

US 2007/0019158 A1    Jan. 25, 2007

(51) Int. Cl.
*A61B 3/10* (2006.01)
(52) U.S. Cl. .................... 351/214; 351/212; 351/213
(58) Field of Classification Search .............. 351/214
See application file for complete search history.

(56) References Cited

U.S. PATENT DOCUMENTS

| 5,512,966 | A | 4/1996 | Snook |
| 5,562,656 | A | 10/1996 | Sumiya |
| 5,886,767 | A | 3/1999 | Snook |
| 6,056,404 | A * | 5/2000 | Kawai et al. ............... 351/237 |
| 6,257,723 | B1 | 7/2001 | Sarver et al. |
| 6,669,684 | B2 * | 12/2003 | Nakamura .................... 606/5 |
| 2003/0189689 | A1 | 10/2003 | Rathjen |

OTHER PUBLICATIONS

International Search Report (PCT/ISA/210) and Written Opinion (PCT/ISA/237) mailed on Dec. 5, 2006.

* cited by examiner

*Primary Examiner*—Jessica Stultz

(57) ABSTRACT

A corneal topography slit image alignment system 10, includes a half-slit projector 14 for projecting half-slit images onto a patient's eye 16. Half-slit images 28 and 30 are aligned into a single slit image. A camera 18 captures an image of the aligned slit image. Processor 20 including a memory 26 connected to the half-slit projector 12 and the camera 18 analyzes the alignment of the half-slit images 28 and 30. An edge detector 22 detects the edges of each captured half-slit image and determines an amount of misalignment of the half-slit images 28 and 30 relative to half-slit images being aligned into a single slit image. This amount of misalignment allows computer processor 20 to correct the three-dimensional coordinates of the slit images obtained by a slit beam system 14.

10 Claims, 2 Drawing Sheets

CORNEAL TOPOGRAPHY SLIT IMAGE ALIGNMENT VIA ANALYSIS OF HALF-SLIT IMAGE ALIGNMENT

BACKGROUND OF THE INVENTION

1. Field of the Invention

The present invention relates to corneal topography slit beam systems. More specifically, the present invention relates to alignment of the slit images obtained from scanning a patient's eye.

2. Description of Related Art

Slit beam systems, such as Bausch & Lomb Incorporated's ORBSCAN II™ topography system are well known in the field of ophthalmology. A slit beam system is described in detail, in the following patents, U.S. Pat. Nos. 5,886,767; 5,512,966; and 6,257,723 all of which are hereby incorporated by reference. Slit beam systems provide a topographical mathematical model or map of a patient's eye. In order to generate the model or map of the eye, the position of the illuminated slit images in three-dimensional space is required. Obviously the more accurately that the position of the slit images is determined, the more accurate the mathematical model will be.

Initial alignment of the eye to the system has always been a serious issue in creating eye models from the image data. Errors in misalignment directly result in errors in both the estimates of optical power and details in the reconstructed eye surfaces, both the anterior corneal surfaces and the posterior corneal surfaces.

It is well known in the art to use half-slit images, which an operator of the slit beam system then manipulates, such that the half-slits are moved to form a single slit image that is centered on the display. This alignment of the half-slit images is used to align the slit beam system to the eye to be measured.

Therefore, if the alignment of the half-slit images could be made to be more accurate, the image data obtained when measuring the eye can then be made more accurate. Errors in the half-slit image alignment directly result in errors in the calculation of the coordinates of the slit images in three-dimensional space.

DETAILED DESCRIPTION OF THE PREFERRED EMBODIMENT

Errors in misalignment of a slit beam system with respect to the eye to be measured directly result in errors in both of estimates of optical power and details in the reconstructed eye surfaces from captured slit images. Historically, a half-slit image has been employed by a practitioner to perform the alignment of the system to the eye, by aligning the half-slits into a single slit image. However, these half-slit images have not been recorded or analyzed by the system for accuracy. By analyzing the manually aligned half-slit images, the quality of alignment of the system and the eventual slit image reconstructions into topographical eye models may be achieved.

The goal of the practitioner is to ensure that the two half-slit images align on top of each other. However, for various reasons good alignment is not always achieved either through user error or through movement of the patient's eye or other factors. By capturing the half-slit images and analyzing the captured image to determine the position of the edges and the vertical positioning of the slits, alignment error by the practitioner can be greatly minimized or even eliminated.

Figure 1:
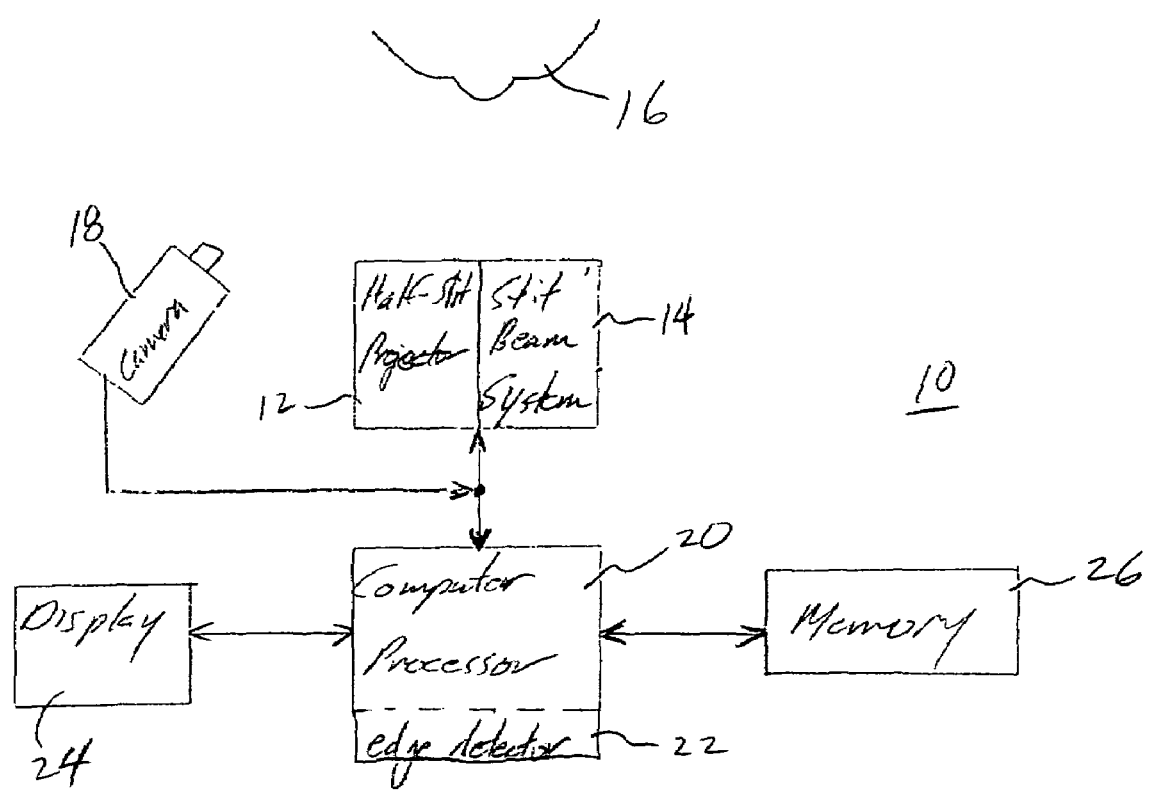
FIG. 1 is a block diagram of a corneal topography slit image alignment system in accordance with the present invention.
Figure 2:
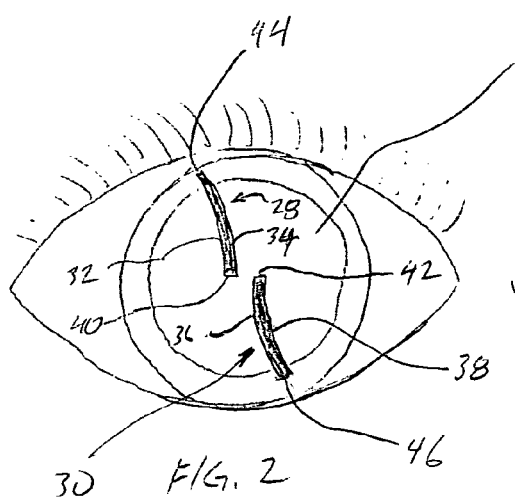
FIG. 2 is a graphical representation of the half-slit images projected onto an eye.

FIG. 1 shows a corneal topography slit image alignment system 10 in accordance with the present invention. System 10 includes a half-slit projector 12 and a slit beam system 14 for projecting the slits onto an eye 16. A camera 18 is provided to capture images of the slits projected onto eye 16. System 10 further includes a computer processor 20, slit beam system 14, and an edge detector 22 forms a part of computer processor 20, or edge detector 22 may be a separate structure, depending on the design requirements. A display 24 is also preferably connected to computer processor 20. Further, a memory 26 is preferably connected to computer processor 20.

Preferably, the half-slit images are acquired by camera 18 after a practitioner has manually aligned the half-slit images. The images are then analyzed to determine the side edges of each half-slit and to determine the top and bottom of each slit. These images should appear in known positions. The difference between the desired known position and the actual detected position of the edges can be used to specify misalignment in three-dimensional space along the x, y, and z-axes. If the eye is misaligned in the z direction, i.e. the eye image is too close or too far away from the camera 18 or the slit beam system 14, the half-slit images will not come together vertically. If the eye is misaligned in the y direction, the slits will not come together horizontally. Finally, if the images are misaligned vertically, then the place that the slits come together will be misaligned from the center of the image.

Referring again to FIG. 1, the half slit projector 12, projects half-slit images, as explained in detailed below, onto a patient's eye 16, wherein the half-slit images are to be aligned into a single slit image. The camera 18 then captures an image of the aligned slit image. Computer processor 20 including memory 26 is connected to the half-slit projector 12 and the camera 18 analyzes the alignment of the half-slit images. The edge detector 22 detects the edges of each captured half-slit image and determines an amount of misalignment of the half-slit images relative to a theoretical half-slit image aligned into a single slit image. This determination of an amount of misalignment allows the computer processor to correct the alignment in three-dimensional coordinates of slit images obtained by the slit beam system 14. This then allows a more accurate eye model to be generated by the system 10.

Figure 3:
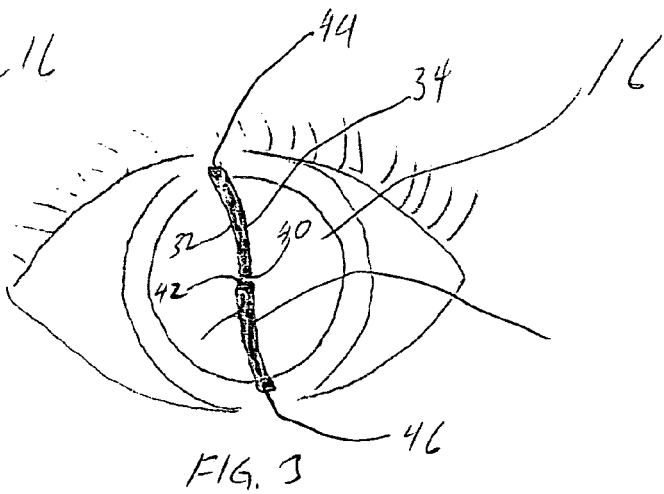
FIG. 3 is a graphical representation of half-slit images aligned on an eye.

Each half-slit image 28 and 30 includes at least two opposing side edges 32 and 34 and 36 and 38 respectively. Each half-slit image 28 and 30 also preferably includes an end edge 40 and 42, as shown. Each half-slit 28 and 30 generally forms half of a single slit when aligned properly each end edge 40 and 42 abuts the other end edge, as shown in FIG. 3. Also, half-slit images 28 and 30 may preferably include top and bottom edges 44 and 46.

Figure 4:
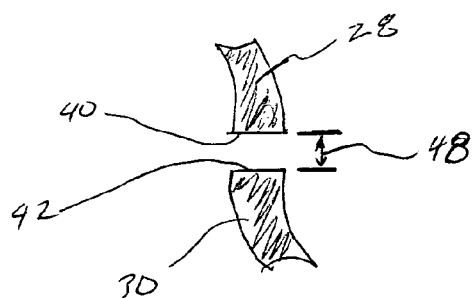
FIG. 4 is a partial graphical representation of half-slit images misaligned in a vertical direction.
Figure 5:
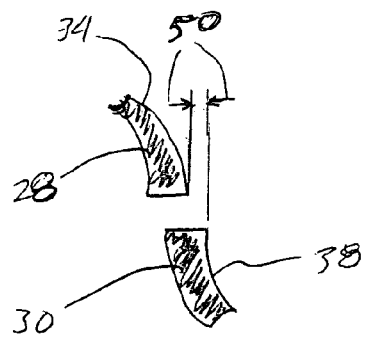
FIG. 5 is a partial graphical representation of half-slit images misaligned in a horizontal direction.

FIG. 4 shows a partial view of slits 28 and 30, wherein a vertical gap, shown at 48, between the end edges 40 and 42, corresponds to a misalignment of the system 10 relative to the eye 16 and the z distance from the camera 18 to the eye 16. The distance of the vertical gap, shown at 48, directly corresponds to the misalignment distance from the eye 16 to the camera 18. The computer processor 20 can then use this misalignment distance to adjust the calculated coordinates of the slit beam images from slit beam system 14 to more accurately determine a topographical map of eye 16.

Similarly, a horizontal separation, shown at arrows 50, between the side edges 34 and 38 of each half-slit image 28 and 30 corresponds to a horizontal or x-axis alignment of the slit images obtained from the slit beam system 14. The distance of the horizontal misalignment, shown at 50, can then be adjusted for by computer processor 20 to more accurately determine the coordinates of the slit beam images obtained from slit beam system 14 to obtain an accurate eye model of eye 16.

Figure 6:
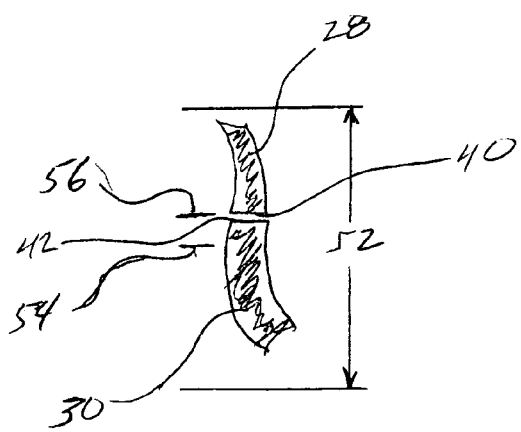
FIG. 6 is a partial graphical representation of a pair of half-slit images misaligned with respect to the center of a field of view of the system.

FIG. 6 again shows a partial graphical representation of half slit images 28 and 30. The distance, shown at 52, can be said to provide the distance of the entire image field and the lines, shown at 54, can be said to represent a center of the image field 52. The misalignment of the center of the aligned half-slit images 28 and 30 can be said to be 56. The amount of off-set or misalignment of the center of the aligned slit images at 56 relative to the center of the image field center at 54 can be said to be a vertical misalignment. The vertical misalignment of a mean of a vertical position of the end edges 40 and 42 from the image center 54 corresponds to a vertical misalignment of the slit images obtained from the slit beam system 14.

In this way, it has been shown that by capturing images of the aligned half-slit images projected on eye 16 for aligning the system 10 to eye 16 errors in the misalignment of the half-slit images can be corrected for and a more accurate eye model of the eye can be constructed from the slit beam images obtained by slit beam system 14.

In use, the half-slit projector 12 will project a pair of half-slit images 28 and 30 onto a patient's eye 16. A practitioner then aligns the half-slit images 28 and 30 into a single slit image as shown in FIG. 3. The camera 18 then captures an image of the aligned half-slit images. Computer processor 20, including memory 26, connected to the half-slit projector 12 and the camera 18 analyzes the alignment of the half-slit images captured by the camera 18. The edge detector 22 then detects the edges of the captured half-slit images and determines an amount of misalignment of the half-slit images relative to the half-slit images being perfectly aligned into a single slit image. Determination of the misalignment of the half-slit images allows a correction of slit images to be obtained by slit beam system 14, which results in a more accurate eye model of eye 16.

I claim:

1. A corneal topography slit image alignment system comprising;
    a half-slit projector for projecting half-slit images onto a patient's eye, wherein the half-slit images are to be aligned into a single slit image;
    a camera for capturing an image of the aligned slit image;
    a computer processor, including memory, connected to the half-slit projector and the camera for analyzing the alignment of half-slit images; and
    an edge detector for detecting edges of each captured half-slit image and determining an amount of misalignment of the half slit images relative to the half-slit images aligned into a single slit image thereby allowing corrections of slit images obtained by a slit beam system.

2. The invention of claim 1, wherein each half-slit image includes at least two opposing side edges and an end edge and wherein each half-slit generally forms half of a single slit when aligned such that each end edge abuts the other end edge.

3. The invention of claim 2, wherein a vertical gap between the end edges corresponds to a misalignment in a distance from the camera of the slit beam system.

4. The invention of claim 2, wherein a horizontal separation between the side edges of each half-slit image correspond to a horizontal misalignment of slit images obtained from the slit beam system.

5. The invention of claim 2, wherein a vertical misalignment of a mean of a vertical position of the end edges from an image center corresponds to a vertical misalignment of the slit image obtained from the slit beam system.

6. A method of determining an amount of misalignment of a pair of half-slit images of a corneal topography slit image system, the method comprising to steps of;
    projecting, with a half-slit projector, a pair of half-slit images onto a patient's eye, wherein the half-slit images are to be aligned into a single slit image;
    capturing, with a camera an image of the aligned half-slit images;
    analyzing, with a computer processor, including a memory connected to the half-slit projector and the camera the alignment of the half-slit images; and
    detecting, with an edge detector, edges of each captured half-slit image and determining an amount of misalignment of the half-slit images relative to the half-slit images aligned into a single slit image thereby allowing a correction of slit images obtained by a slit beam system.

7. The method of claim 6, wherein the detecting step includes detecting at least two side edges and an end edge of each half-slit and wherein each half-slit generally forms half of a single slit when aligned, such that each end edge abuts the other end edge.

8. The method of claim 7 further including a step of determining a vertical gap distance between the end edges, wherein the vertical gap distance corresponds to a misalignment of a distance from the camera of the slit beam system.

9. The method of claim 7 further including a step of determining a horizontal separation distance between the side edges of each half-slit image, wherein the horizontal separation distance corresponds to a horizontal misalignment of slit images obtained from the slit beam system.

10. The method of claim 7 further including a step of determining a vertical misalignment distance from a mean vertical position of the end edges from an image center, wherein the vertical misalignment distance corresponds to a vertical misalignment of slit images obtained from the slit beam system.

* * * * *